US007892493B2

(12) United States Patent
Weekamp

(10) Patent No.: US 7,892,493 B2

(45) Date of Patent: Feb. 22, 2011

(54) FLUID SAMPLE TRANSPORT DEVICE WITH REDUCED DEAD VOLUME FOR PROCESSING, CONTROLLING AND/OR DETECTING A FLUID SAMPLE

(75) Inventor: Johannes Wilhelmus Weekamp, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 46 days.

(21) Appl. No.: 12/298,951

(22) PCT Filed: Apr. 23, 2007

(86) PCT No.: PCT/IB2007/051475

§ 371 (c)(1),
(2), (4) Date: Oct. 29, 2008

(87) PCT Pub. No.: WO2007/125468

PCT Pub. Date: Nov. 8, 2007

(65) Prior Publication Data

US 2009/0130766 A1 May 21, 2009

(30) Foreign Application Priority Data

May 1, 2006 (EP) .................................. 06113342

(51) Int. Cl.
*G01N 33/00* (2006.01)

(52) U.S. Cl. .......................... 422/81; 422/58; 422/68.1; 422/99; 422/100; 422/102; 422/103; 436/174; 436/180

(58) Field of Classification Search ....................... None
See application file for complete search history.

(56) References Cited

U.S. PATENT DOCUMENTS

| | | | | |
|---|---|---|---|---|
| 5,833,926 | A | 11/1998 | Wurzel et al. | |
| 6,929,239 | B1 * | 8/2005 | Colin et al. | 251/115 |
| 6,960,437 | B2 | 11/2005 | Enzelberger et al. | |
| 2001/0012612 | A1 | 8/2001 | Petersen et al. | |
| 2001/0029983 | A1 | 10/2001 | Unger et al. | |
| 2003/0057391 | A1 | 3/2003 | Krulevitch et al. | |
| 2003/0143754 | A1 * | 7/2003 | Lum et al. | 436/180 |

(Continued)

FOREIGN PATENT DOCUMENTS

DE 10238585 B3 4/2004

(Continued)

*Primary Examiner*—Yelena G Gakh
*Assistant Examiner*—Christopher A Hixson

(57) ABSTRACT

A fluid sample transport device with reduced dead volume for processing, controlling and/or detecting a fluid sample, includes a substrate having an upper surface with at least one processing, controlling and/or detecting element. At least one flexible membrane is arranged on the upper surface of the substrate. The fluid sample transport device further includes at least one plunger and/or actuating element for actuating an up and/or down movement of the flexible membrane to cause a fluid flow and/or to stop a fluid flow. A cover plate is arranged on the upper outer surface or lower outer surface of the flexible membrane. The cover plate includes at least one through going hole and/or cut-out for receiving a plunger and/or actuating element, so that movement of the plunger and/or actuating element causes a pump and/or valve action of the adjacent arranged flexible membrane area to cause a fluid flow in a channel temporally formed by expansion of the flexible membrane. The temporally formed channel is between the upper surface of the substrate and the lower surface of the flexible membrane.

16 Claims, 13 Drawing Sheets

U.S. PATENT DOCUMENTS

2004/0151629 A1 8/2004 Pease et al.
2005/0170493 A1 8/2005 Patno et al.
2005/0249605 A1 11/2005 Kane et al.

FOREIGN PATENT DOCUMENTS

WO 2005098289 A1 10/2005
WO 2006098817 A1 9/2006
WO 2007027928 A1 3/2007
WO 2007093939 A1 8/2007

* cited by examiner

FLUID SAMPLE TRANSPORT DEVICE WITH REDUCED DEAD VOLUME FOR PROCESSING, CONTROLLING AND/OR DETECTING A FLUID SAMPLE

BACKGROUND OF THE INVENTION

This invention relates to a fluid sample transport device with a reduced dead volume for processing, controlling and/or detecting a fluid sample. This invention relates in particular to a molecular diagnostic application with a reduced dead volume. The fluid sample transport device with reduced dead volume according to the present invention is preferably used in molecular diagnostics.

The biotechnology sector has directed substantial effort towards developing miniaturized fluid sample transport devices such as microfluidic devices, often termed labs-on-a-chip (LOC) or micro total analyses systems (microTAS), for sample manipulation and analysis. These systems are used for detection and analyses of specific bio-molecules, such as DNA and proteins.

In general micro-system devices contain fluidic, electrical and mechanical functions, comprising pumps, valves, mixers, heaters, and sensors such as optical-, magnetic- and/or electrical sensors. A typical molecular diagnostic assay includes process steps such as cell lyses, washing, amplification by PCR, and/or detection.

Integrated microfluidic devices need to combine a number of functions, like filtering, mixing, fluid actuation, valving, heating, cooling and optical, electrical or magnetic detection, on a single template. Following a modular concept the different functions can be realised on separate functional substrates, like silicon or glass. The functions need to be assembled with a microfluidic channel system, which is typically made of plastic. With small channel geometries this way of integration becomes a very challenging process. The interfaces between the substrates and the channel plate need to be very smooth and accurate, and the channel geometries need to be reproducible, while the functional substrates should have a minimum footprint for cost efficiency. Especially with functions, which need a fluidic as well as an electric interface, the separation of the wet interface is critical. Bonding techniques must be compatible with the biochemical reagents and surface treatments present on the functional substrates.

US-A1 2003/0057391, incorporated by reference, discloses a low power integrated pumping and valving array which provides a revolutionary approach for performing pumping and valving operations in micro fabricated fluidic systems for applications such as medical diagnostic microchips. This approach integrates a lower power, high-pressure source with a polymer, ceramic, or metal plug enclosed within a micro channel, analogous to a micro syringe. When the pressure source is activated, the polymer plug slides within the micro channel, pumping the fluid on the opposite side of the plug without allowing fluid to leak around the plug. The plugs also can serve as micro valves.

However, the pump system of US-A1 2003/0057391 does not provide a sufficient small dead volume and does not provide an optimized fast fluid transport. Further, the plugs must have a positive fitting to avoid sample fluid leakage thus the low power integrated pumping and valving arrays can not be provided at low vertical range of manufacture.

In the last decade, considerable research efforts have been made to the development of microfluidic system devices in order to integrate more functions but at the same time reducing the analyze samples volumes of liquid.

Despite this effort, there is still a need for a fluid sample transport devices such as a microfluidic system device, microfluidic bio chips, often termed Bio Flips, LOCs and microTASs, to overcome at least one drawback of the prior art mentioned above. Further, there is a need to develop technologies that lead to total integration of peripheral functions onto single microchips, including innovative low power/pressure sources for on-chip fluidic manifolds that allows analyzing samples in small volumes of liquid as well as providing more economical use of reagents and samples. In particular there is a need for a fluid sample transport device with an optimized reduced dead volume to a minimum.

SUMMARY OF THE INVENTION

The fluid sample transport device according to the present invention, also referred as microfluidic device, allows the integration of many functions for molecular diagnostics applications. The fluid sample transport device according to the present invention may analyze samples in small volumes of liquid, providing more economical use of reagents and samples, and in some cases dramatically speeding up assays.

Further, the fluid sample transport device for molecular diagnostic applications according to the present invention allows a lateral flow of the fluid sample. This allows a vertical integration of sensors and other devices for the treatment, processing and/or analysis of a fluid sample of an assay. To integrate a large number of functions on the fluid sample transport device for molecular diagnostic applications according to the present invention it is suggested to integrate all or at least most of these functions on at least one substrate Furthermore, the fluid sample transport device according of the present invention provides a fluid sample transport with an optimized dead volume reduced to a minimum, preferably about zero.

According to the present invention a fluid sample transport device with reduced dead volume for processing, controlling and/or detecting a fluid sample, comprising:

a substrate, wherein the upper surface of said substrate comprises at least one processing, controlling and/or detecting element;

at least one flexible membrane, wherein the flexible membrane is arranged on the upper surface of said substrate;

at least one plunger and/or actuating element for actuating an up and/or down movement of the flexible membrane to cause a fluid flow and/or to stop a fluid flow;

at least one cover plate arranged on the upper outer surface or lower outer surface of the flexible membrane, wherein the cover plate comprises at least one through going hole and/or cut-out for receiving a plunger and/or actuating element, so that movement of said plunger and/or actuating element causes a pump and/or valve action of the adjacent arranged flexible membrane area to cause a fluid flow between the upper surface of said substrate and the lower surface of said flexible membrane; and wherein at least one channel to direct the fluid sample flow on the substrate is temporally formed by the flexible membrane.

The fluid sample transport device according of the present invention can be preferably a micro fluidic device. The fluid sample transport device according to the present invention can be used as Lab-on-chip (LOC) or as Micro Total Analyses Systems (micro TAS) in for example molecular diagnostics applications.

As used herein, the term “detection means” or “detecting element” refers to any means, structure or configuration, which allows one to interrogate a fluid sample within the sample-processing compartment using analytical detection techniques well known in the art. Thus, a detection means may include one or more apertures, elongated apertures or grooves which communicate with the sample processing compartment and may allow an external detection apparatus or device to be interfaced with the sample processing compartment to detect a fluid sample, also referred as analyte, passing through the fluid sample transport device.

The term "fluid sample" is used to refer to any compound or composition, which can be pumped through the temporally formed channel system. The "fluid sample" is preferably a liquid.

The term "channel" or "channel system" as used in the present invention means a conduit through which a fluid flow can be directed, for example to a desired cavity, recess and/or area located on the substrate.

A channel or channel system can be connected with at least one cavity, recess and/or area located on the substrate where the fluid can be for example processed, collected, controlled and/or detected.

A temporally channel is formed by expanding or stretching the flexible membrane, so that the flexible membrane forms for a example a curve like tunnel on the substrate through that a fluid sample can flow.

The term "temporally" means with respect to the channel, that the channel is not permanent formed. This means that a temporally formed membrane channel can be returned to a non-channel design, such as a planar or flat membrane design contacting the substrate.

In general, the membrane contacts completely the substrate. In case a temporally membrane channel is formed, the section of the membrane that forms the temporally channel does not contact the surface of the substrate.

The terms "through going hole" and "through going cut" with respect to the cover plate means that the through hole as well as the through cut extend from the upper surface of the cover plate to the lower surface of the cover plate (from one side to the other side).

Thus, it can be preferred, that the substrate has at least one cavity, recess and/or area located on the substrate where the fluid sample can be processed, collected, controlled and/or detected.

It can be preferred, that the lower surface of the cover plate facing to the membrane is a plane and/or smooth surface. This form of the lower surface of the cover plate reduces the dead volume with respect to the temporally formable channel system to a minimum.

It can be further preferred, that the lower surface of the cover plate facing to the membrane has no cavity and/or recess, except at least one through going hole and/or at least one through going cut.

It can be preferred also, that the lower surface of the cover plate completely contacts the upper surface of the membrane facing to the cover plate, except at this areas where the cover plate comprises a through going hole and/or through going cut.

BRIEF DESCRIPTION OF THE DRAWINGS

FIG. 12*a* top view of a thin foil 30.

FIG. 12*c* top view of a thin foil 30 mounted on a base substrate 2.

DETAILED DESCRIPTION OF THE INVENTION

Figure 1:
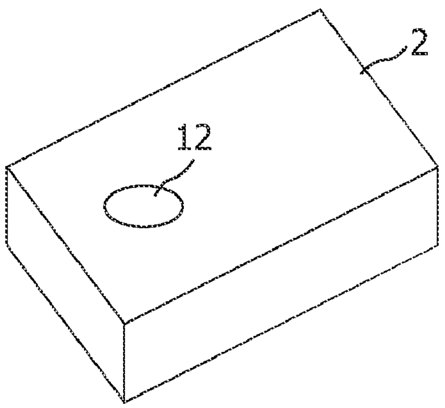
FIG. 1 is a sectional side view of a substrate with a cavity for receiving a fluid sample.

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. Thus, for example, reference to "a fluid" may include mixtures, reference to "a heat device" includes two or more such devices, reference to "a temporally formed channel" may include more than at least one of such temporally formed channels, and the like.

It has thus been shown that the present invention has provided a new approach for performing pumping and valving operations by a flexible membrane in micro fabricated fluid systems for applications such as medical diagnostic microchips, wherein the flexible membrane forms a temporally channel through which a fluid sample can be forced through. By the use of the flexible membrane of the fluid sample transport device, also referred as cartridge, can be effectively utilized as a pump for fluid transport or as a control valve. The flexible membrane has a variable operational capability, it can be used for forming a temporally formed channel, and it can have a valve function or a pumping function. Thus, a chip scale integrated sample preparation system can be produced utilizing the invention.

The fluid sample transport device can be designed such, that a number of same or different fluid sample processing, detecting and/or controlling steps can be carried out separate, simultaneous and/or subsequent thereon.

It is preferred that the fluid sample transport device comprises a disposable cartridge comprising a substrate covered with a membrane.

It can be preferred that the processing, controlling and/or detecting element are located at the substrate. The substrate can be build up of a base substrate, whereby the upper surface of the base substrate is covered with at least one thin foil, also referred as thin layer. On the substrate and/or on the thin film at least one reagent, circuit, chip and the like can be integrated. It may be preferred that the base substrate is covered with a number of thin foils, such as two, three, four or more.

Further, the fluid sample transport device can comprise at least one temporally formed channel or a temporally formed channel system, whereby the temporally channel is formed by a flexible membrane. The section of the temporally formed channels can be degenerate to a plane membrane contacting the surface of the substrate.

The volume of a temporally channel formed of a flexible membrane for receiving and/or transporting a fluid sample may have a volume of 0.1 $mm^3$ to 2000 $mm^3$, preferably 0.5 $mm^3$ to 1000 $mm^3$ and more preferably 1 $mm^3$ to 50 $mm^3$.

The maximum height of a temporally formed channel, measured from the upper surface of the substrate, may in the range of 5 micron to 500 micron, preferably of 10 micron to 250 micron, further preferred of 20 micron to 100 micron and more preferred of 30 micron to 50 micron.

The maximum width of a temporally formed channel may in the range of 0.1 micron to 10000 micron, preferably of 5 micron to 2000 micron, further preferred of 50 micron to 500 micron and more preferred 100 micron to 200 micron.

According to a preferred embodiment of the present invention the substrate as such does not possess a permanent channel or a permanent channel array, through which a fluid sample flow can be forced.

However, it can be beside the temporally formed membrane channel/s still preferred that the substrate provide in addition at least one permanent channel arranged on said substrate.

The substrate can comprise at least one area, recess and/or cavity where the fluid sample is treated, such as heated, cooled, controlled, reacted, measured and/or analyzed.

It is preferred, that the substrate has at least one cavity for receiving a fluid sample and/or a reagent. The cavity/cavities can be located on the upper or lower surface of the substrate of the fluid sample transport device.

It can be preferred that the temporally formed channel or a temporally formed channel system connects area/s and/or cavity/cavities. The area/s and/or cavity/cavities may comprise at least one element for processing, controlling and/or detecting at least one fluid sample.

The substrate material can be selected from the group comprising glass, ceramic, silicon, metal and/or polymer.

On top of the substrate a flexible membrane is arranged. The size of the flexible membrane may be selected so that the flexible membrane completely or partly covers the upper surface of the substrate. It can be preferred also that the flexible membrane wraps around the substrate. It is most preferred that the flexible membrane covers the fluid sample transport device at least on all areas where a pump or valve action is desired and/or a temporally channel needs to be formed for directing the fluid sample to a cavity or area, where the fluid sample is detected, controlled and/or processed. It can be further preferred that the flexible membrane covers the processing, controlling and/or detecting areas as well. However, it is most preferred that the flexible membrane completely covers or wraps the upper surface of the substrate.

An up and down movement of said flexible membrane cause a pump action or valve action so that fluid located in said temporally formed channels is transported or stopped on the substrate. An up movement of the flexible membrane can cause a suction function and a down movement of the flexible membrane can force a fluid sample flow and/or causes a valve function.

Plungers, actuator elements or the like can be used to apply pressure and/or vacuum to the flexible membrane. Thus, plungers and/or actuator elements may be selected such that they have a pressure, vacuum and/or lift function with respect to the flexible membrane. In particular, plungers, actuator elements or the like can be selected such that they have a lift up and/or lift down function, to move up and/or down the flexible membrane. Such means may comprise suction means, pumping means, and/or mechanical means.

The plungers, actuating elements, such as inserts, initiate fluid transport by actuating the flexible membrane causing a pump and/or valve action, so that liquid is forced into the temporally formed channel/s on the substrate and forced to the next treatment step of the assay. The fluid actuation system by the membrane according to the present invention is fast and provides a minimized dead volume up to about zero.

For example, to close or minimize a temporally formed channel and/or to cause a pump or valve action of the flexible membrane pressure or vacuum can be directed to the upper surface of the flexible membrane. Due to the action of the pressure mean/s the flexible membrane is moved downwardly to the substrate at least at areas where the pressure is subjected. Using vacuum can move the flexible membrane up, so that a temporally membrane channel can be formed at least at areas where the vacuum is subjected to. Further, a pump and/or valve action can be caused to the fluid sample.

The plungers and/or actuator elements are not in contact with the fluid sample since the flexible membrane has a fluid sealing function. The plungers and/or actuator elements actuate the upper surface of the flexible membrane at specific areas so that defined areas of the flexible membrane can be lifted up or down only.

It is preferred that the flexible membrane surface is liquid tide sealed at least at areas adjacent to areas where the flexible membrane has a pump action, valve action and/or adjacent to areas where the flexible membrane is desired to form a temporally channel to avoid a liquid sample leak. In particular, it is preferred, that the membrane is connected to the substrate leakage free, so that fluid sample cannot accidental be lost.

The flexible membrane can be fixed further by means of a cover plate, also referred as fixture. The cover plate can comprise at least one through going hole, cut and/or cut-out. The hole, cut and/or cut-out can be used to insert a plunger element and/or a actuating element so that the flexible membrane can be moved up and down to cause a pump and/or valve action with respect to the actuated flexible membrane and/or to form a temporally flexible membrane channel. Further, at least one through going hole of the cover plate can be used for cooling actions.

The cover plate can have the form of a housing, encompassing at least three outer surfaces of a substrate. It is preferred that the cover plate can have at least one cut-out.

However, it is preferred that the through going cut/s and/or the through going hole/s forms a linked channel system in said cover plate.

Further, it may be preferred that the cover plate is disconnectable arranged on the substrate covered or wrapped with a flexible membrane (cartridge). Since the cover plate can be disconnectable arranged on the substrate with the flexible membrane, it is possible to reuse the cover plate. The substrate covered or wrapped with the flexible membrane, i.e. the cartridge, is contaminated after use with the fluid sample, so that the cartridge, substrate with the flexible membrane, is disposable after used.

In case a disconnectable cover plate is used, it is possible to exchange cover plates with different hole, cutting and/or channel structure design. This allows for example, that a fluid sample can differentially be processed and/or analyzed on the same cartridge.

The cover plate can be mounted on the substrate with a flexible membrane thereon by fixing means such as clamps, connecting means, screws and the like.

However, it is also possible that the cover plate is fixed on the substrate with the flexible membrane, i.e. the cover plate cannot be removed from the substrate with the flexible membrane.

Preferably, the membrane is fixed on the substrate at least on all areas, where the flexible membrane is not allowed to form a temporally chamber/s and/or temporally channel/s. However, it is possible, that the membrane is fixed on the substrate at least along the edges of said temporally chamber/s and/or temporally channel/s. In order to fix the membrane liquid tight on the substrate at said edges or said areas, the membrane can be clamped between the cover plate and the substrate. However, it is also possible that the membrane is fixed by means of an adhesive or the like.

It seems to be clear for an expert, that areas or section/s of the flexible membrane intended to form a temporally chamber/s and/or temporally channel/s are not fixed.

In order to receive an up-movement of the flexible membrane, in particular the membrane of a temporally formed channel, it is preferred that the cover plate comprises at least one through going hole, through going cut and/or a recess faced to the flexible membrane surface. The structure of through going hole/s, through going cut/s and/or a recess/es of the cover plate is designed so, that a fluid sample can be directed by temporally formed channels, plungers and/or actuating elements to the desired area/s or region/s where the fluid sample is detected, controlled and/or processed.

The term recess means a hole or cut which is not a through going hole or through going cut. For example, the recess can receive the flexible membrane part of a temporally formed flexible membrane channel.

Thus, it is possible to use a cover plate with a channel structure or recess structure surface, so that a temporally formed flexible membrane channel can be received in that channel. A fluid sample flow can be caused in said temporally formed flexible membrane channel on the substrate. However, fluid sample does not contact the channel or recess of the cover plate, since the fluid is directed between the lower surface of the temporally formed flexible membrane channel and the upper surface of the flexible membrane.

At least one through going hole or cut of the cover plate can be connected to a vacuum and/or pressure device, in order to form a temporally channel of the flexible membrane and/or to actuate the pump and/or valve function of said flexible membrane to cause a fluid sample flow.

To receive the temporally formed channel of the flexible membrane it is preferred that the cover plate arranged above the upper surface of the membrane comprises at the surface facing to the upper surface of said membrane at least one channel or channel structure. The channel or channel structure of the cover plate is designed in such a way that a fluid sample flow can be directed on the substrate to at least one cavity, recess and/or area, where the fluid sample is detected, controlled and/or processed.

Further, the cover plate can comprise at least one through going hole and/or cut into a plunger and/or an actuating element can engage or connected for actuating an up and/or down movement of the flexible membrane in order to form a temporally channel, to cause a fluid sample flow through a channel and/or to stop a fluid flow on the substrate.

Therefore, it is not necessary that the cover plate has a channel or channel structure on the surface facing to the flexible membrane, because it is also possible that the cover plate has at least one through going hole and/or cut into which the flexible membrane can engage. Furthermore, a cover plate is preferred having a channel or channel structure as well as at least one through going hole and/or cut into which the flexible membrane can engage at an up movement.

The channel structure and/or recess can be formed in said cover plate by general known techniques. It is preferred that the cover plate is made of a plastic material. According to the present invention, it is possible that the outer lower surface of the cover plate is coated with a polymer layer, so that the channel/s and/or recess/es can be formed in said polymer layer.

In case of using a plunger/s it is preferred that the lower surface size of the plunger/s corresponds with the shape of the surface below, so that a down movement of the plunger contacting the flexible membrane causes a fluid pressure and/or valve action of the flexible membrane. The plunger can be connected with the upper surface of the flexible membrane, the plunger can be part of the membrane, and/or the plunger fits so in a hole, cut, so that an up and down movement of the plunger actuate the pump and/or valve action of the flexible membrane. If the plunger is part of the flexible membrane, the plunger can be hollow so that a squeezing cause a pump and/or valve action. The plungers can be made of plastic, metal, glass and/or ceramic material.

Due to the pump and/or valve effect of the flexible membrane at defined areas, i.e. at areas where the flexible membrane is not fixed in its position, fluid sample can be transported through a micro channel system temporally formed by the flexible membrane to a desired cavity, recess and/or area. Thus, a fluid sample can be transported through the temporally formed flexible membrane on the substrate to a number of different places, where the fluid sample is detected, controlled and/or processed.

Therefore, the fluid sample transport device of the present invention may allow a multiple forward and backward fluid sample transport through the temporally formed flexible membrane channel/s.

Further, the integrated flexible membrane of the fluid sample transport device of the present invention provides a fast fluid transport, a minimized pump and valve dead volume, preferably the dead volume is near zero as well as a low vertical range of manufacture. The minimized dead volume is one benefit of the fluid sample transport device according to the present invention.

In the present invention the total dead volume (in volume %) of all channels through which the fluid sample is transported on the substrate can be preferably ≧0% and less than 10%, preferably less than 1%, more preferably less than 0.1% and most preferably less than 0.01%. The dead volume in vol. -% is based on the total channel volume through which the fluid sample can be transported on the substrate.

Further, the total dead volume (in volume %) of the fluid sample transport device through which the fluid sample can be transported on the substrate, comprising channels, cavities, recesses and/or areas, can be preferably ≧0% and less than 10%, preferably less than 1% and more preferably less than 0.1%.

The flexible membrane as used according to the present invention is preferably liquid tight, so that liquid fluid does not penetrate the flexible membrane during operation. It may be preferred that the membrane is flexible and elastic. Suitable membrane materials are polymers, preferably natural or synthetic rubbers.

It can be preferred that the flexible membrane has a thickness of 1 μm to 500 μm, preferably 10 μm to 300 μm and most preferred 50 μm to 200 μm. If the membrane is to thin there is a danger of deterioration of the membrane, which may result in leakage of the fluid sample. However, if the membrane is to thick, there is a danger of malfunction of the pump and /or valve effect of said membrane with respect to fluid transportation. Further, the formation of a temporally channel is disabled if the membrane is to thick. Most preferred is a rubber membrane having a thickness between 50 μm and 200 μm.

The fluid sample transport device can comprise processing, controlling and/or detecting elements. The processing, controlling and/or detecting elements are preferably arranged on and/or in the substrate. Said processing, controlling and/or detecting elements comprising heaters, sensors, detectors etc. can be integrated by means of thin film technology. In general, the fluid sample transport device according to the present invention can comprise electronic device/s such as thin-film electronic devices.

The substrate can consist of at least on layer. However, it is preferred that the substrate of the fluid sample transport device according to the present invention comprises at least two layers.

The substrate may include a plurality of thin-film layers forming the substrate. Preferably the substrate comprises a base layer covered at least on one outer surface with a thin-film layer. Suitable thin-film layers comprising at least one electronic device selected from the group comprising electrodes for applying electric fields, sensors, transducers, optical-based devices, acoustic-based devices such as piezo-based oscillators for applying ultrasonic energy, electric field-based devices, and magnetic field-based devices, among others. Sensors may be temperature sensors such as thermocouples, thermistors such as resistive heating devices, p-n junctions, degenerative band-gap sensors, etc., light sensors for example photodiodes or other optoelectronic devices, pressure sensors for example, piezoelectric elements, fluid flow rate sensors for example, based on sensing pressure or rate of heat loss from a heating element, and electrical sensors, among others.

Preferably, electronic device/s comprise processing, controlling and/or detecting means, also referred herein to as elements. Processing means comprising electronic device/s for temperature control of the fluid, electronic device/s for heating and/or cooling the fluid, electronic device/s configured to sense or modifies a property of the fluid. Further, a processing mean, also referred as processing element, comprises a reagent.

The electronic device/s may be disposed so that the electronic devices can participate in sample processing and/or monitoring the fluid sample in the channel system, areas, recesses and/or cavities where a fluid sample flow can be directed. Accordingly, electronic devices may be disposed more efficiently in relation to processing areas, enabling more flexibility in how samples are manipulated. Furthermore, devices that participate in related aspects of fluid sample processing, such as heaters/coolers and temperature sensors, may be disposed in a more cooperative spatial relationship to modify and sense the temperature of substantially the same fluid volume.

Electronic devices, such as thin-film electronic devices and methods to integrate such devices are disclosed in US-A1 20040151629 and incorporated herein by reference.

Preferably, the processing, controlling and/or detecting elements, comprising at least an electrode, a sensor, a transducer, a heating element, an optical-based device, such as wave guide, a laser, an acoustic-based device, an electric field-based device and/or a magnetic field-based device. Processing elements comprising for example cell lyses, washing, mixing, amplification by PCR and/or detection.

In more detail, the fluid sample transport device provides an array of temporally formable channels, wherein the temporally channels are formed by a flexible membrane arranged on a substrate. The flexible membrane can be covered on or wrapped on the substrate. Further, a cover plate can be mounted, preferably disconnectable mounted, on the upper surface of the membrane, so that the membrane is sandwiched between the substrate and the disconnectable cover plate.

The cover plate has at least one recess or cut in order to receive a temporally formed channel. Thus, the cover plate has a negative structure of the channel structure into which a temporally formed channel can engage. The cover plate structure faced to the upper surface of the membrane can have two functions. The first function of the cover plate is to fix the membrane on the substrate. Therefore, it can be preferred that the lower surface of the cover plate has a plane surface in order to secure the flexible membrane on the surface. The second function of the cover plate is to receive the expansion of the temporally formed flexible membrane channel. To receive a temporally formed flexible membrane channel the cover plate comprises at least one recess on its lower surface and/or at least one cut into which the expanded flexible membrane channel can engage.

A fluid sample can flow on the substrate through the temporally formed flexible membrane channel. Since the temporally formed flexible membrane channel has a defined direction given by the recess/es and/or through going cut/s of the cover plate. Thus, a fluid sample flow can be directed on the substrate to at least one cavity, recess and/or area, where the fluid sample is detected, controlled and/or processed.

An actuating element can be inserted into the through going cut/s. The actuating element can be an insert, a pressure source and/or vacuum source. An up and/or down movement of the insert or pressure/vacuum of the pressure/vacuum source can cause a corresponding movement of the adjacent arranged flexible membrane. For example, a down movement of an insert located in the cut can cause a fluid flow in the temporally formed channel below, since the pressure force of said actuating element causes a downward movement of the temporally formed flexible membrane channel to the substrate. The same applies to a pressure/vacuum source. Further, a cover plate can provide at least one through going hole into which a plunger can engage or an actuating element can be connected.

A fluid sample transport device according to the present invention with a low vertical range of manufacture comprises at least two elements: (a) a substrate with integrated analytical, electrical and/or optical function, such as reagents, sensors and/or actuators, and if necessary the electrical infrastructure, (b) a flexible membrane, which covers or wraps around the substrate, wherein the flexible membrane forms at least one temporally channel to direct and/or control the fluid sample flow, and (c) a cover plate with at least one through going hole or through going cut to receive a plunger and/or actuating element having a valve and/or pump function with respect to the fluid sample.

According to a preferred embodiment of a fluid sample transport device according to the present invention, the device comprises a substrate with a cavity for receiving a fluid sample, whereby the substrate is wrapped with a flexible membrane. On top of the substrate covered or wrapped with the flexible membrane a cover plate is disconnectable mounted, so that the flexible membrane is sandwiched between the substrate and the cover plate. The cover plate comprises a first through going hole for receiving a first plunger. The position of the lower opening of said first through going hole of the cover plate corresponds to the upper opening of the fluid sample cavity, so that an down movement of the plunger contacts the flexible membrane below and fluid sample is pushed out of the cavity of the substrate. It is preferred that the plunger part, which contacts the membrane and engages into the cavity, has a positive fit, so that the dead volume with respect to the cavity design is at a minimum, preferably zero. Further, adjacent to the first through going hole a through going cut is formed in said cover plate into which an insert is arranged. At the end part of said through going cut a second through going hole is formed in said cover plate, which receives a second plunger. Downward movement of said first plunger pushes the fluid sample out of the cavity. The fluid sample flow causes the formation of a temporally flexible membrane channel, whereby the expansion of the flexible membrane is received by the through going cut. Downward movement of the insert arranged in the through going cut causes a fluid flow of the fluid sample in direction to the second plunge, which is pushed up by the upper membrane surface contacting the plunger, since the flexible membrane is pressed down to the upper surface of the substrate. Alternative, up and down movement of the first plunger, insert and second plunger causes a pump and/or valve action so that the fluid sample can be transported on the substrate through a temporally formed channel rear and forward. It is preferred that the substrate provides at least one processing, controlling and/or detecting element.

To combine a number of detecting, processing and/or controlling steps on a substrate it is preferred that the cover plate can have a plurality of through going holes and through going cuts and/or a plurality of recesses at its lower surface.

The substrate can comprise at least one cavity, recess and/or area located on the substrate, where the fluid sample is detected, controlled and/or processed. The cavities, recesses and/or areas are located on the substrate so that it corresponds with the design of the cover plate in order to achieve a directed and controlled fluid sample transport on the substrate. The fluid sample flow through temporally formable channel system is achieved, controlled and directed by means such as plungers, inserts and actuating elements having a pump and/or valve function.

According to a further embodiment of the present invention the fluid sample transport device comprises a cover plate with a plurality of through going holes and through going cuts and/or a plurality of recesses at its lower surface. This fluid sample transport device provides a directed and controlled fluid sample transport to a number of cavities, recesses and/or areas located on the substrate, where the fluid sample is detected, controlled and/or processed thereon.

The mentioned above embodiment provides a fluid sample transport device where a fluid sample can be multiple detected, controlled and/or processed. Further, it is possible, that fluid samples can be differently treated on the substrate depending on the flow path on the substrate. For example, this kind of fluid sample transport device can be used for different assays, since a fluid sample flow can be directed to miscellaneous regions on the substrate for a specific treatment.

However, a fluid sample transport device in which a single fluid sample is subjected to a number of processing, controlling and/or detecting steps is most preferred.

The fluid sample transport device according to the present invention is preferably a disposable cartridge. The support plate may be reusable or disposable. Most preferred is that the cover plate can be reused, but the substrate covered or wrapped with the membrane is disposable. Thus, the fluid sample transport device can be made of a disposable cartridge covered with a reusable cover plate.

The fluid sample transport device or cartridge, in particular the substrate can have a connector on at least one surface side, which provides electrical contact, for example with a control system.

FIG. 1 shows a substrate 2 with a cavity 12 for receiving a fluid sample. The substrate 2 can be based on a plurality of thin-film layers (not shown) with processing, controlling and/or detecting elements (not shown).

In general, processing, controlling and/or detecting elements are preferably arranged on and/or in the substrate. Said processing, controlling and/or detecting elements comprise electronic devices such as heaters, sensors, detectors etc., which can be integrated by means of thin film technology. Suitable electronic devices are electrodes for applying electric fields, sensors, transducers, optical-based devices, acoustic-based devices such as piezo-based oscillators for applying ultrasonic energy, electric field-based devices, and magnetic field-based devices, among others. Also, the processing, controlling and/or detecting elements can comprise chemical compounds as used for example for cell lyses, washing, and amplification by PCR and the like.

Figure 2A:
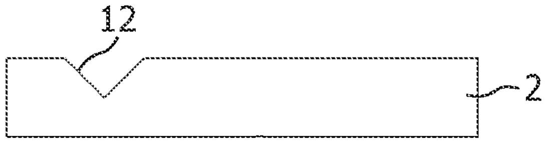
FIG. 2*a* is a sectional side view of the substrate of FIG. 1 with a cavity for receiving a fluid sample.
Figure 2B:
FIG. 2*b* is a sectional side view of the substrate of FIG. 1 with a cavity containing a fluid sample.
Figure 2C:
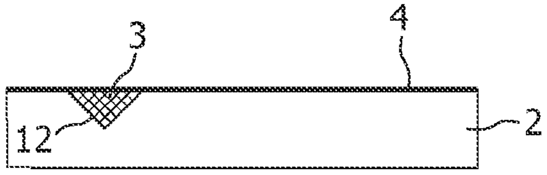
FIG. 2*c* is a side view of the substrate of FIG. 1 with a cavity containing a fluid sample and a flexible membrane.

FIGS. 2*a*, 2*b* and 2*c* show the build up of a disposable cartridge. FIG. 2*a* shows the sectional side view of the substrate 2 with a cavity 12 of FIG. 1. FIG. 2*b* shows the sectional side view of the substrate 2 with a cavity 12 of FIG. 2*a*, wherein the cavity is filled with a fluid sample 3. FIG. 2*c* shows the sectional side view of the substrate 2 with a cavity 12 filled with a fluid sample 3 of FIG. 2*b*, whereby the substrate 2, cavity 12 and fluid sample 3 is covered with a flexible membrane 4. The fluid sample 3 can be injected through the flexible membrane 4 into the cavity via a syringe. As an alternative, the substrate 2 can possess a port (not shown). The fluid sample 3 can be introduced into the cavity 12 via said port.

As an alternative, it is preferred that the flexible membrane 4 wraps around the substrate 2 (not shown in FIG. 2*c*), which provides an easy and good fixation of the flexible membrane 4 on the substrate 2.

FIGS. 3*a*, 3*b*, 3*c*, 3*d* and 3*e* shows the directed fluid flow of a fluid sample 3 on the substrate 2 actuated by pump and valve action of plungers 5*a*/5*b* and an insert 9 of a fluid sample transport device 1 according to the present invention.

Figure 3A:
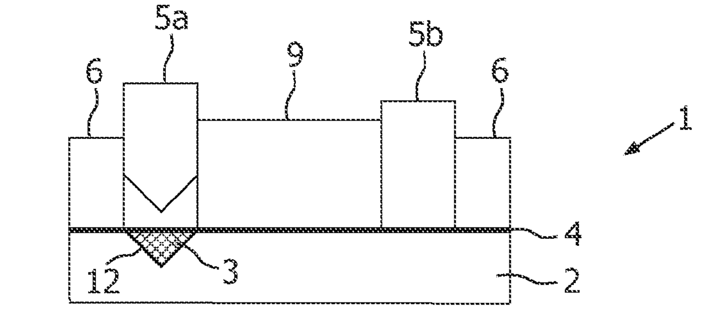
FIG. 3*a* is a sectional side view of a fluid sample transport device.

FIG. 3*a* shows in a sectional side view a fluid sample transport device 1 composed of a substrate 2 with processing, controlling and/or detecting steps (not shown), the substrate comprises further a cavity 12 containing a fluid sample 3, a flexible membrane 4 wrapped on the substrate 2 and covering the fluid sample 3 leaked tight, a cover plate 6 containing through going holes for receiving the plungers 5*a* and 5*b* and a through going cut 8 for receiving an insert 9. The plunger 5*a*, the insert 9 and the plunger 5*b* are adjacent arranged, respectively. The fluid sample 3 can be injected through the flexible membrane 4 into the cavity via a syringe, after the plunger 5*a* has been removed. In case, the plunger 5*a* is of a soft material and/or the plunger 5*a* is hollow, it is possible to inject the fluid sample 3 through the plunger 5*a* and the flexible membrane 4 via a syringe. As an alternative, the substrate 2 can possess a port access (not shown), through that the fluid sample 3 can be introduced into the cavity 12. As can be seen from FIG. 3*a* the plunger 5*a*is in a moved up position. Further, the upper section of the plunger 5*a* has been adapted to the design of the cavity, so that it precisely fits into the cavity 12 (positive fit) in order to reduce the dead volume to a minimum, preferably to about zero.

Figure 3B:
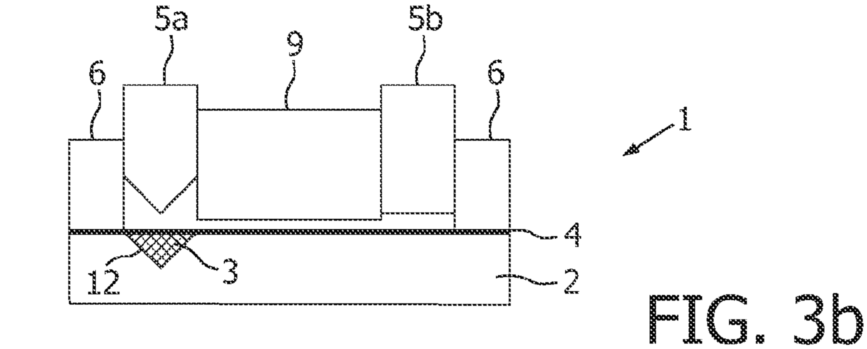
FIG. 3*b* is a sectional side view of a fluid sample transport device ready for fluid flow.

FIG. 3*b* shows the same fluid sample transport device 1 of FIG. 3*a*, except that plungers 5*a*/5*b* and insert 9 are in a moved up position.

Figure 3C:
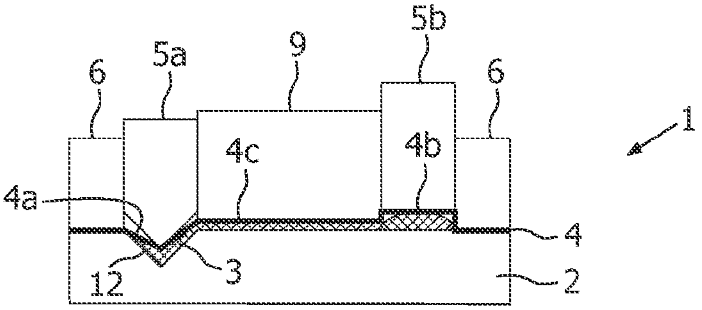
FIG. 3*c* is a sectional side view of a fluid sample transport device at fluid flow.

FIG. 3*c* shows the same fluid sample transport device 1 of FIG. 3*b*, except that plunger 5*a* is moved down. It can be seen that the lower end of the plunger 5*a* contacts the flexible membrane region 4*a*, so that the flexible membrane 4*a* is pressed down and engaged into the cavity 12. Due to the pump action of the plunger 5*a* with respect to the membrane 4 the fluid sample 3 is forced out of the cavity 12 and the flexible membrane section 4*c* forms a temporally channel due to the expansion of the membrane 4 through that the fluid sample 3 can flow, whereby a flexible membrane chamber 4*b* in the through going hole below the lower end of the plunger 5*b* is formed in that the fluid sample 3 collects.

Figure 3D:
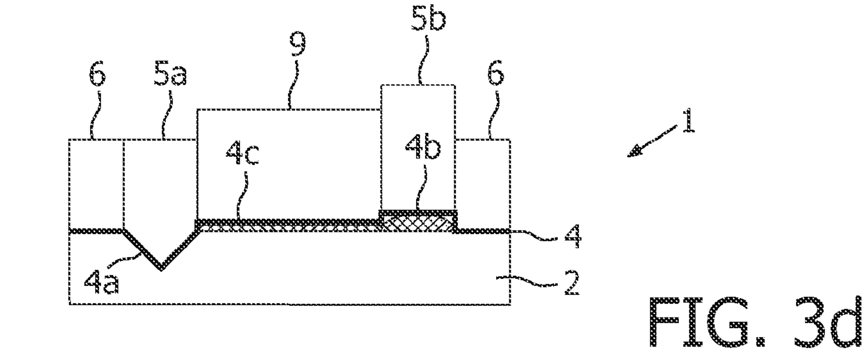
FIG. 3*d* is a sectional side view of a fluid sample transport device at fluid flow.

FIG. 3*d* shows the same fluid sample transport device 1 of FIG. 3*c*, wherein the plunger 5*a* contacting the membrane 4*a* has been completely moved down and fits precisely into the cavity 12. It can be seen from FIG. 3*d* that the fluid sample 3 is completely forced out of the cavity 12, so that the dead volume with respect to the cavity 12 is about zero. The fluid sample 3 is forced due to the pump action of the plunger 5*a* through the temporally formed flexible membrane channel 4*c* in the direction of the temporally formed membrane chamber 4*b*.

Figure 3E:
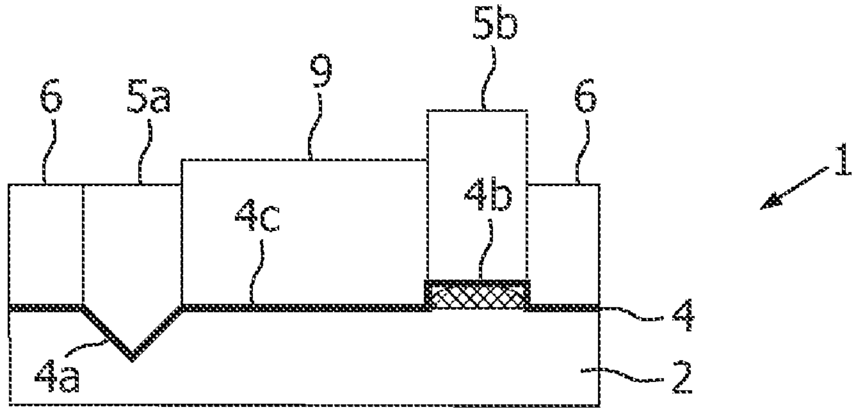
FIG. 3*e* is a sectional side view of a fluid sample transport device after fluid flow.

FIG. 3*e* shows the same fluid sample transport device 1 of FIG. 3*d*, wherein the insert 9 contacting the membrane 4*c* has been completely moved down to the substrate, so that the temporally formed flexible membrane channel 4*c* has be removed and the fluid sample 3 has been completely transferred into the temporally formed membrane chamber 4*b*. Since the substrate 2 does not have micro channels, no fluid sample is lost and the dead volume with respect to the channel system of the fluid sample transport device 1 is about zero.

It can be further seen from FIG. 3*a* to 3*e* that the fluid sample does not contact the cover plate 6 or parts thereof like plungers 5 or inserts 9. Thus, the cover plate 6, plungers 5 and inserts 9 can be reused. However, the cartridge comprising the substrate and the membrane is disposable, since the cartridge only is contaminated with the fluid sample.

Figure 4A:
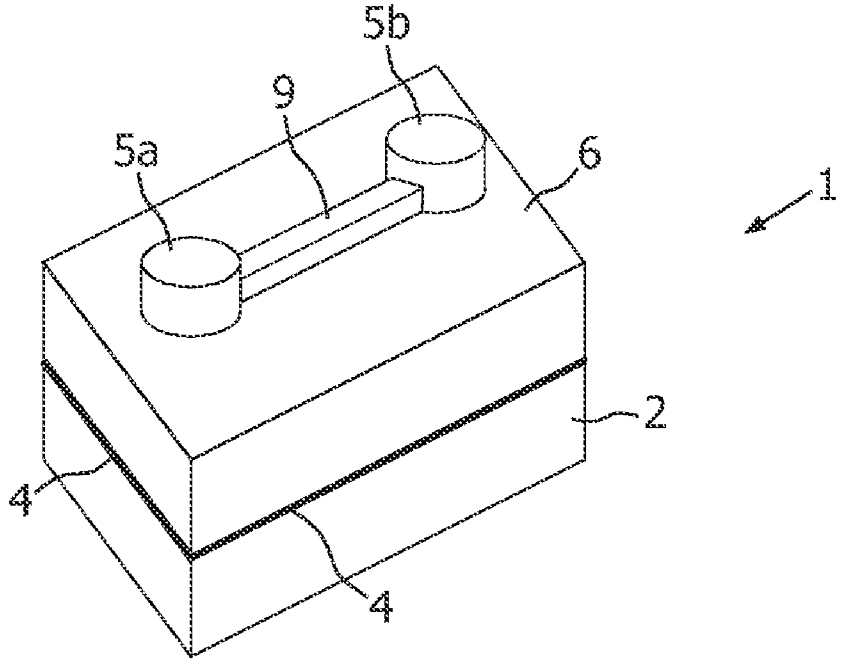
FIG. 4*a* is a sectional side view of the fluid sample transport device.

FIG. 4*a* shows a fluid sample transport device 1 according to the present invention. The upper surface of the substrate 2 is covered with a flexible membrane 4. The membrane 4 is sandwiched between said substrate 2 and the cover plate 6. The cover plate 6 comprises a first through going hole into that a plunger 5*a* engages. Adjacent to the first through going hole, a through going cut 8 is arranged into that an insert 9 is engaged. At the opposite site of the through going cut 8 and adjacent thereto a second through going hole is arranged at the cover plate 6 into that a plunger 5*b* engages. An up- and/or down movement of the plungers 5*a*/5*b* and the insert 9 force a directed fluid sample flow on the substrate below the flexible membrane 4. A temporally channel can be formed by stretching the flexible membrane 4 through which a fluid sample can flow through, The expanded flexible membrane of the temporally formed channel can engage into the lower section of the through going cut 8 of the cover plate 6. Pressing down the insert 9 causes a pump action of the membrane of the temporally formed channel, whereby said channel is returned to a flat membrane 4. Thus, a forward and/or backward fluid sample flow can be cause by actuating the flexible membrane due to the pump and valve function of the plungers 5*a*/5*b* and the insert 9. The fluid sample 3 can be injected through the flexible membrane 4 into the cavity via a syringe. As an alternative, the substrate 2 can possess a port (not shown). The fluid sample 3 can be introduced into the cavity 12 via said port. Processing, controlling and/or detecting areas as well as devices are not shown. Further, the cartridge, in particular the substrate, can have a connector (not shown) on at least one surface side, which provides electrical contact, for example with a control system (not shown).

Figure 4B:
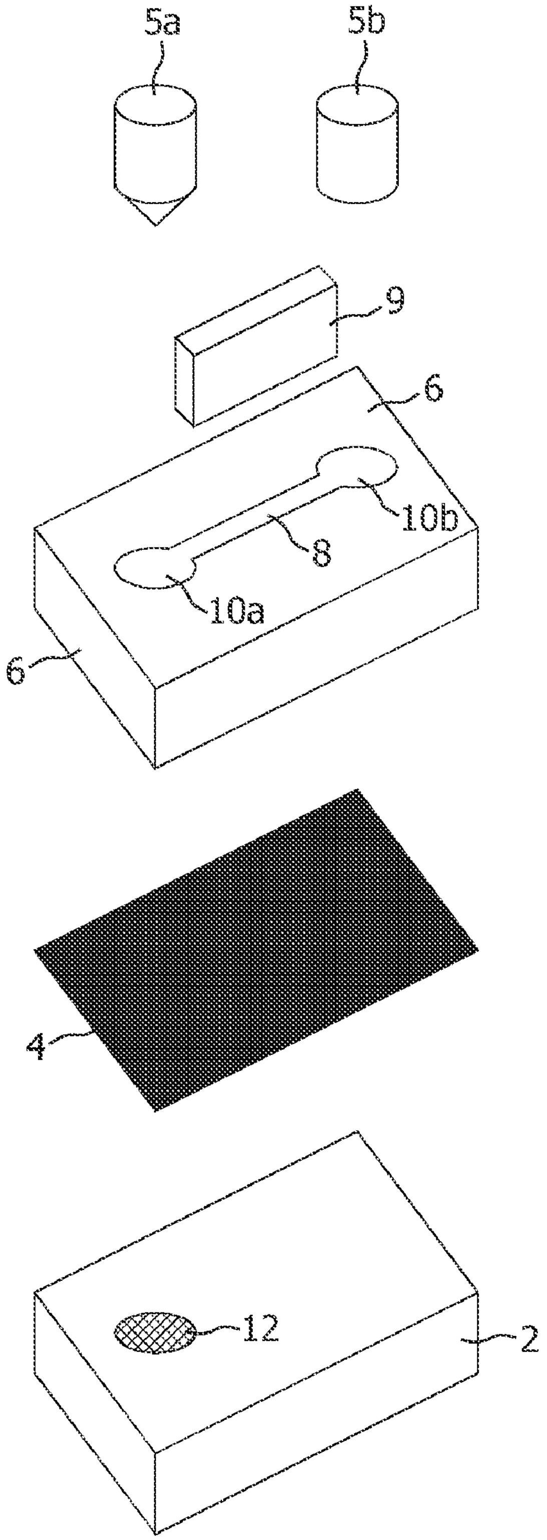
FIG. 4*b* shows the components of the fluid sample transport device of FIG. 4*a*.

FIG. 4*b* shows the parts of a fluid sample transport device 1 of FIG. 4*a* comprising plungers 5*a*/5*b*, an insert 9 a cover plate 6 with a first and second through going hole and a through going cut 8 adjacent arranged between, a flexible membrane 4 and a cover plate 2 with a cavity 12 for receiving a fluid sample probe 3. The lower part of the plunger 5*a* has been adapted to the design of the cavity, so that it precisely fits into the cavity 12 (positive fit) in order to reduce the dead volume to a minimum, preferably to about zero. The lower part of the plunger 5*a* and the insert 6 has been adapted to the design of the upper surface of the substrate 2 below, so that the dead volume can be reduced to a minimum, preferably to about zero. Processing, controlling and/or detecting areas as well as devices are not shown.

Figure 5:
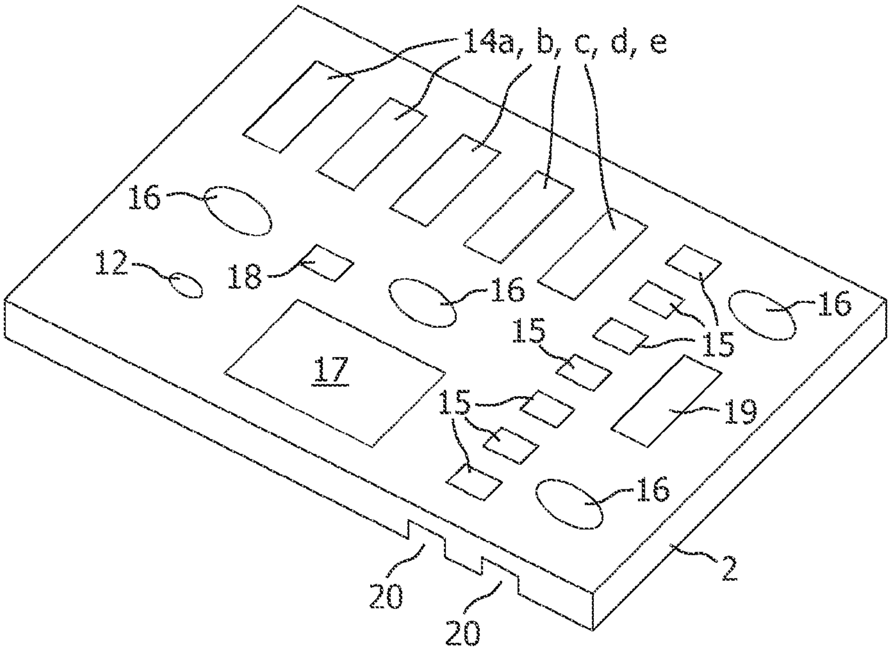
FIG. 5 is a side view of a substrate with PCR chamber and integrated temperature sensor and heater elements.

FIG. 5 shows a substrate 2 with a cavity 12 for receiving a fluid sample 3 and areas comprising a variety of processing, controlling and/or detecting elements 20. In more detail, the substrate comprises chemical reagents containing chambers 14. The fluid sample can be treated and/or processed in said chambers 14 or the chemical reagent/s can be pump out of the chambers, so that the fluid sample can be processed or treated therewith at a different area on said substrate. The reagent/s in the chambers 14*a, b, c, d, e* can be same or different. The chambers can have the design of a recess or cavity formed on the upper surface of the substrate 2. However, it is possible also that the reagents are arranged on a plane area of the substrate 2. The substrate 2 comprises further PCR-chamber/s 15, preferably with heater/s and sensor plate/s. In order to provide a pump and/or valve action to cause or stop a fluid flow of the fluid sample on the substrate 2 to the desired areas, where the fluid sample is detected, controlled and/or processed, the substrate 2 can comprise deepening/s 16 into that the flexible membrane 2 (not shown) can be engaged due to the action of a plunger 5 (not shown). Further, a waste chamber 17 can be arranged on the substrate 2 to receive used reagents, processed fluid sample or the like. Also, a lysis and/or purification treatment and processing element 18 can be arranged on said substrate 2, where the fluid sample can be treated or processed. For detecting, a detection array 19 can be arranged on the substrate 2. The detection array 19 can be arranged in a deepening, such as cavity or recess, of the substrate 2. The substrate can possess at its outer surface at least one cavity 20 or recess 20 for cooling and/or heating purposes. Thus, an easy and fast cooling or heating action can be achieved, since the substrate material is thinned at this area/s 20.

Figure 6:
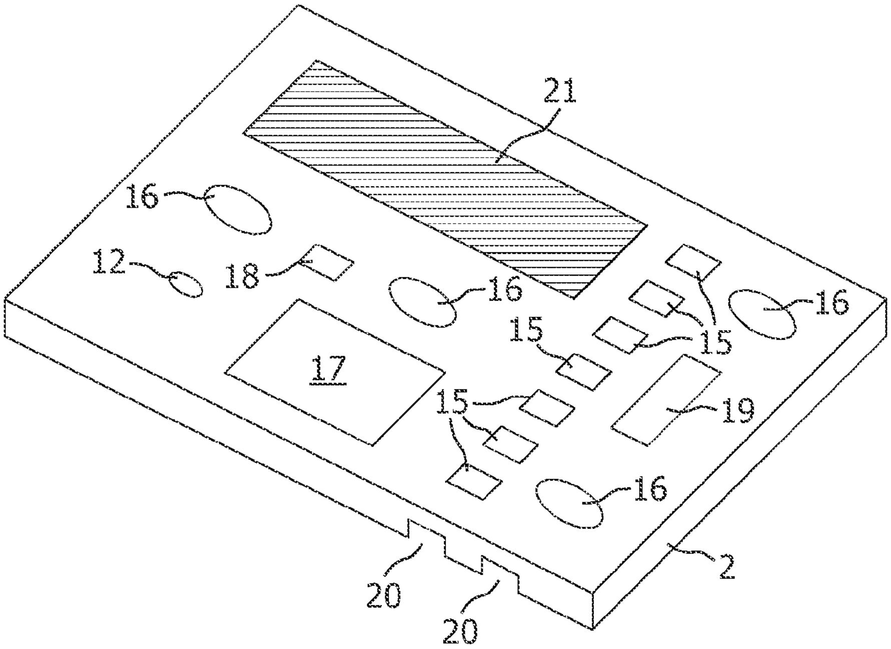
FIG. 6 is a side view of a substrate of FIG. 5 with an aluminium cover.

FIG. 6 shows the same substrate 2 as described in FIG. 5, whereby the area of the chemical reagents containing chambers 14*a, b, c, d, e* is covered with a thin foil 21, for example a thin aluminium foil 21. To release the reagent/s contained in the reagents containing chambers 14*a, b, c, d, e*. The thin foil can for example be ripped open by use of a plunger 5 (not shown) or actuating element 9 (not shown).

Figure 7:
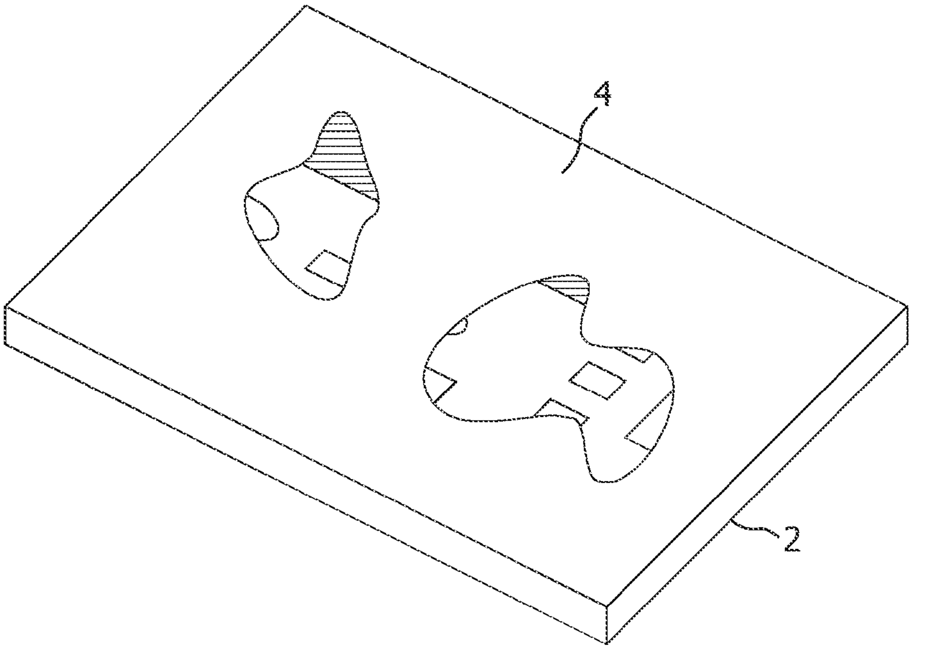
FIG. 7 is a sectional side view of the substrate of FIG. 6 wrapped around with a flexible membrane.

FIG. 7 shows a substrate 2 according to FIG. 6 wrapped with a flexible membrane 4. The cartridge, in particular the substrate, can have a connector (not shown) on at least one surface side, which provides electrical contact, for example with a control system (not shown).

Figure 8:
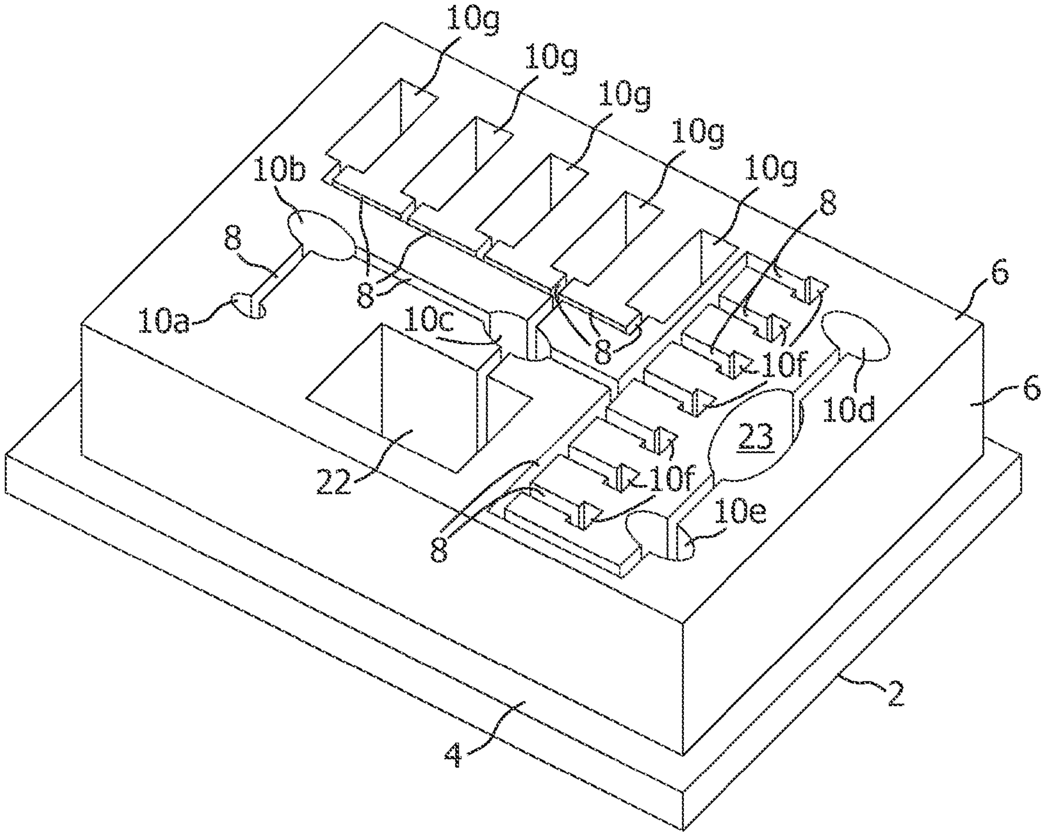
FIG. 8 is a sectional side view of the substrate of FIG. 7 with a cover plate.

FIG. 8 shows a cartridge of a substrate 2 wrapped with a flexible membrane 4 according to FIG. 7 covered with a cover plate 6. The cover plate 6 is arranged on the upper surface of the membrane 4. The cover plate 6 is disconnectable attached to said substrate 2 wrapped with the flexible membrane 4. Thus, the cover plate 6 can be reused, whereas the cartridge can be disposable. The cover plate 6 has a number of through going holes 10*a-g* and through going cuts 8. The position of the lower opening of the through going hole 10*a* corresponds to the cavity 12 for receiving a fluid sample 3 (compare FIG. 5). The position of each of the lower openings of the through going holes 10*b-e* correspond to each of the deepening 16 of the substrate 2 (compare FIG. 5) into that the flexible membrane 2 (not shown) engages due to the action of a plunger 5 (not shown). Further, the positions of the lower openings of the through going holes 10*f* correspond to the upper openings of the PCR-chamber/s 15 located on the substrate 2 (compare FIG. 5) and the positions of the lower openings of the through going holes 10*g* correspond to the openings of the reagent/s containing chambers 14*a, b, c, d, e* (compare FIG. 5). The through going holes 10*a-g* receiving plungers 5 (not shown), whereas the through going cuts 8 receiving inserts 9 (not shown). The lower section/s of the through going cuts adjacent to the flexible membrane/s are for receiving a temporally formed channel of an expanded flexible membrane. The through going cuts 8 and the through going holes 10*a-g* forms a linked channel system in said cover plate 6. Further, the cover plate 6 has a waste chamber 22. The lower opening of the waste chamber 22 corresponds to the waste chamber 17 arranged on the substrate 2 (not shown). Thus, waste liquid and/or treated fluid sample and the like can be removed via the waste chamber 22. As an alternative, via the waste chamber 22 it may be possible to bring in a reagent or fluid. A port to bring in the fluid sample 3 (not shown) can be located on the lower surface of the substrate 2 or located at a side surface of the substrate 2, preferably in a near proximity to the cavity 12. The opening 23 of the cover plate 2 allows a visible inspection of the detection array 19 arranged on the substrate 2 (compare FIGS. 5 and 6).

Figure 9:
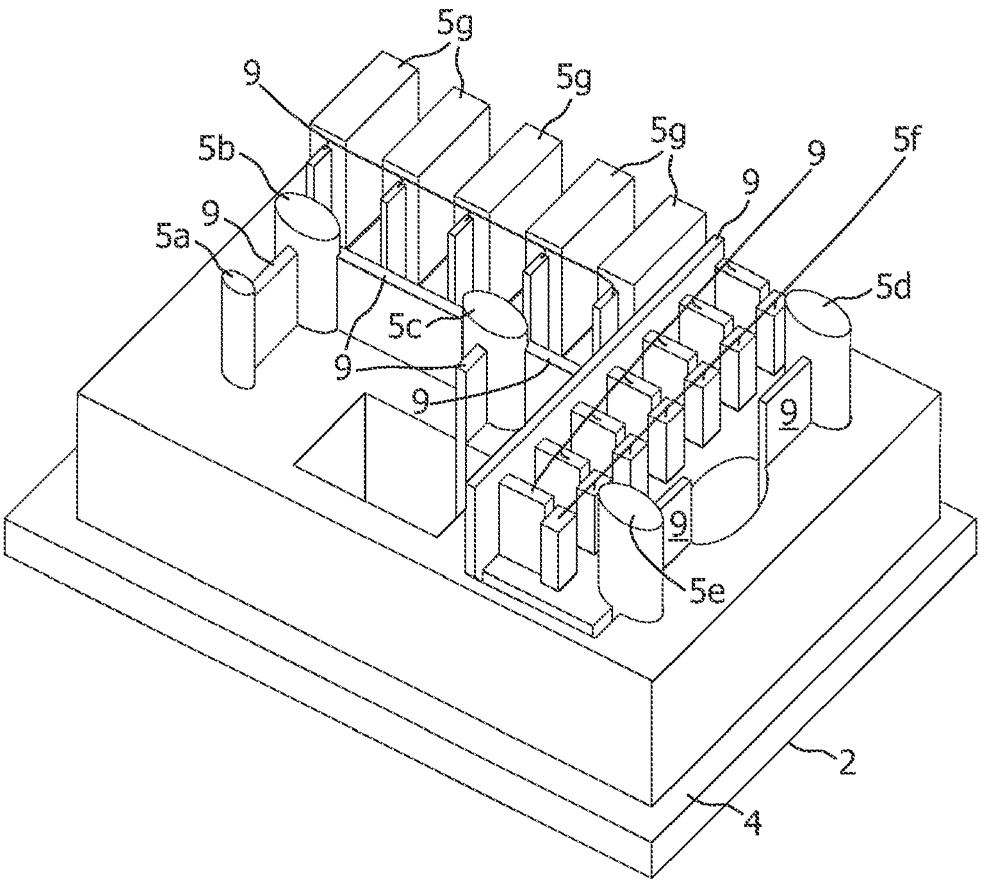
FIG. 9 is a sectional side view of the substrate of FIG. 8 with plungers and actuating elements.

FIG. 9 shows a fluid sample transport device according to the present invention based on a cartridge of a substrate 2 wrapped with a flexible membrane 4 and covered with a cover plate 6 according to FIG. 8. Plungers 5*a* to 5*g* are placed in the through going holes 10*a* to 10*g* respectively. The inserts 9 are placed in the through going cuts 8. The plungers 5*a* to *g* and inserts 9 can be moved up und down in order to enable a directed fluid sample flow on the substrate. The plungers 5*a* to 5*f* have a pump and valve function. The plungers 5*g* can function as a punch to break the thin foil 21 to release the desired reagent/s contained in the reagents containing chambers 14*a, b, c, d, e*. Since the design of the lower end part of said plungers 5*g* correspond to the shape of the reagent chambers, the dead volume with respect to the reagent chamber is reduced to a minimum, preferably about zero. Thus, the reagent, preferably a liquid can be completely brought out of the reagent chamber 14. Alternatively, a fluid sample 3 can be directed to at least one of said reagent chambers 14*a, b, c, d, e*. After the fluid sample 3 has been treated therewith, the fluid sample can be completely removed by actuating the corresponding plunger 5*a*. It is possible that the fluid sample 3 can be treated with a variety of reagents on said substrate 2 or a number of different fluid samples can be treated with a reagent.

A fluid sample 3 can be brought into the cavity 12 (not shown) via a syringe through the membrane adjacent to the lower opening of the through going hole 10*a*. Alternatively, the fluid sample 3 can be brought into the cavity 12 via a port, preferably arranged at a closed proximity of the cavity 12 (not shown). The port can be designed so, that it can receive a sample container (not shown). It is preferred, that the sample container is constructed so, that the fluid sample can be completely transferred into the cavity 12 via the port (not shown).

The through going cuts 8 and the through going holes 10*a-g* forms a linked channel system in said cover plate 6. Thus, due to the pump action of the plunger 5*a* fluid sample 3 can completely be forced out of the cavity 12. The adjacent arranged insert 9 moves up, so that a temporally membrane channel is formed to receive the fluid sample 3, whereby the expanded flexible membrane section 4 engages into the lower section of the corresponding cut 8. Pressing down said insert 9 and opening the plunger 5*b* degenerate the temporally formed membrane channel, so that the fluid sample is collected at the deepening 16 (compare FIGS. 5 and 6). Pressing down the plunger 5*b* and lifting up the insert 9 located between the plungers 5*b* and 5*c* causes a fluid sample flow into the formed temporally channel below said insert. The plungers 5*b* and 5*c* at down position have a valve function, so the fluid sample is completely collected in the formed temporally membrane channel. It is clear for an expert, that due to the pump and valve function of the plungers 5*a* to 5*g* and inserts 9 the fluid sample flow can be directed on the substrate to the desired area/s, where the fluid sample is processed, treated and/or controlled, thus needs not to be further illustrated.

Since the section of the temporally formed channels can be degenerate to a plane membrane, the dead volume with respect to the channel system of the cartridge can be reduced to a minimum, preferably about zero.

Figure 10A:
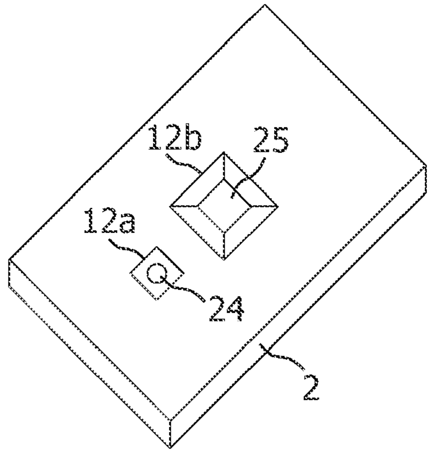
FIG. 10*a* is a sectional top view of a substrate with an integrated sensor chip.

FIG. 10*a* shows a top view of a substrate 2 with a first cavity 12*a* at its upper surface comprising a reagent 24, preferably a freeze-dried reagent, and a second cavity 12*b* comprising an integrated chip 25, preferably a GMR sensor chip, (GMR=Giant Magneto Resistance), as a detecting element.

Figure 10B:
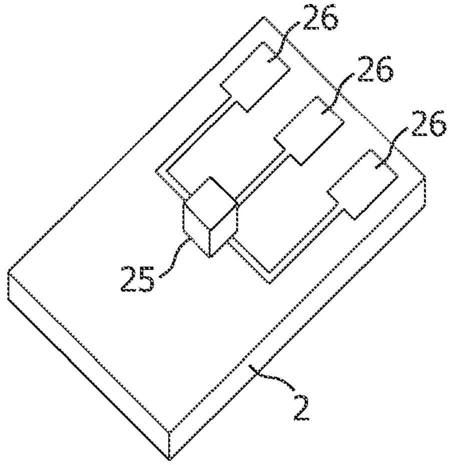
FIG. 10*b* is a sectional rear view of the substrate of FIG. 10*a*.

FIG. 10*b* shows the rear view of the substrate 2 of FIG. 10*a*. On the lower surface the lower part of the chip 25 can be seen. Further electrical contact pads/interface 26 are located on the lower surface of the substrate 2 at an end portion adjacent to a side edge. The contact pads 26 are connected via wires to the sensor chip 25.

Figure 11A:
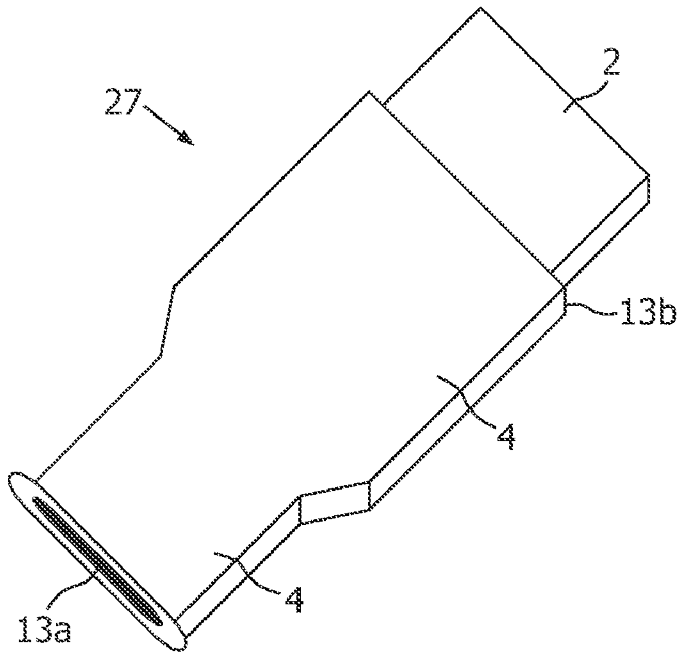
FIG. 11*a* is a sectional top view of a substrate of FIG. 10*a* with a wrapped tube flexible membrane.

FIG. 11*a* shows a top view of a cartridge 27 based on the substrate of FIG. 10*a*, whereby the main part of the substrate 2 is circumference wrapped with a flexible membrane 4. The wrapped around, flexible membrane 4 contacts the substrate 2. However, the membrane 4 does not completely cover the substrate, at least an end part of the substrate 2 is not covered by said membrane 4. The flexible membrane 4 looks like a mouthpiece of an air balloon with two openings 13*a* and 13*b* at opposite ends.

Figure 11B:
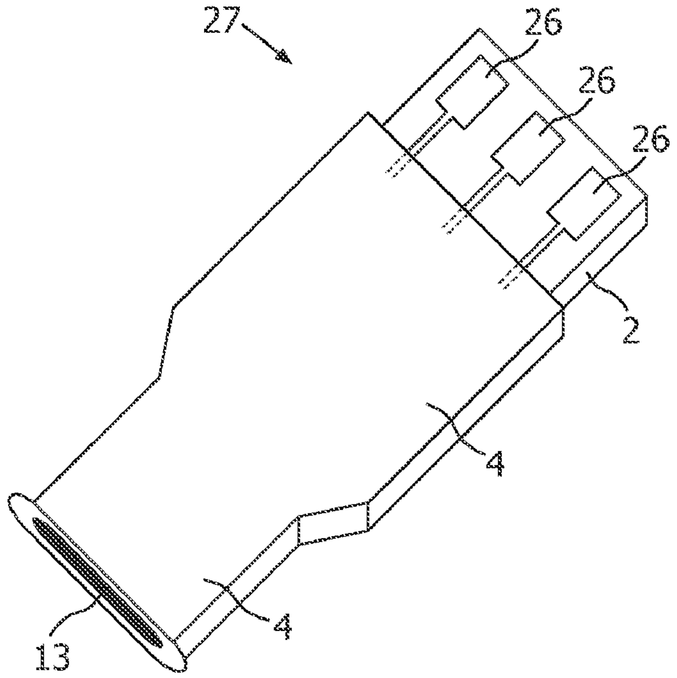
FIG. 11*b* is a sectional rear view of the substrate of FIG. 11*a*.

FIG. 11*b* shows the rear view of the cartridge 27 of FIG. 11*a*. The electrical contacts/interface 26 can be seen on the lower surface of the substrate 2 at the end portion, which is not covered by the membrane 4.

Figure 11C:
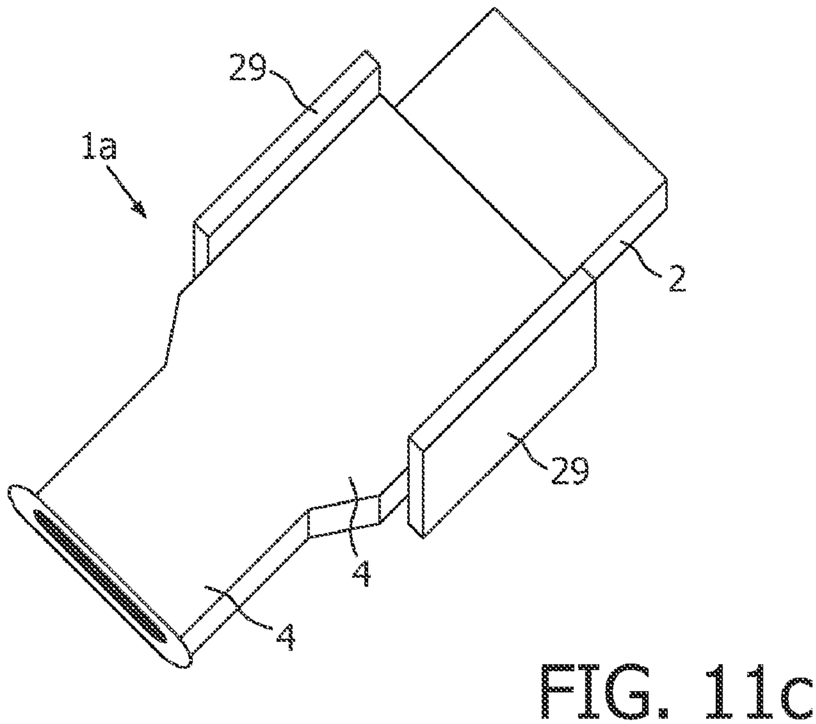
FIG. 11*c* is a sectional top view of the substrate of FIG. 11*a* in a housing.

FIG. 11*c* shows a top view of a fluid transport device 1*a* based on the cartridge 27 of FIG. 11*a*, whereby the cartridge 27 is arranged in a cover plate having the form of a housing 29. The housing 29 encompasses the cartridge 27 at the lower surface and the side surfaces. The housing 29 do not cover the upper surface of said cartridge 27, thus the housing 29 is open at its upper surface.

Figure 11D:
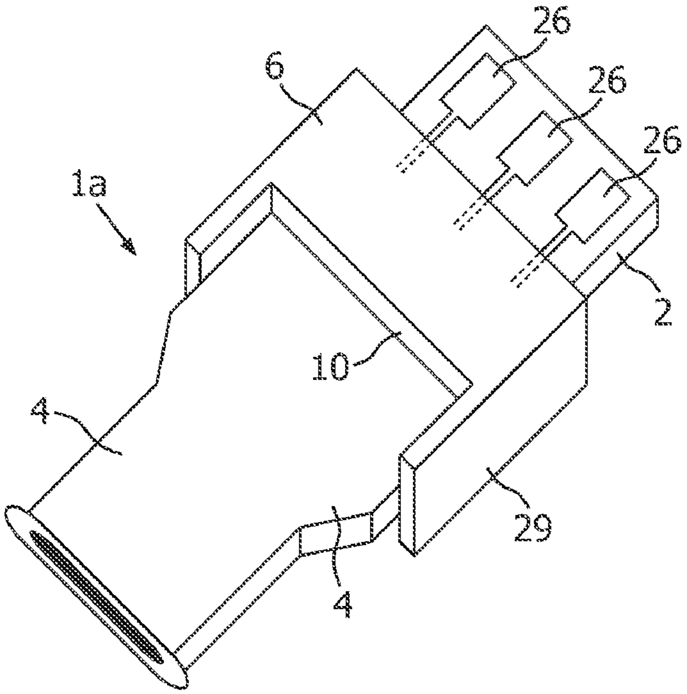
FIG. 11*d* is a sectional rear view of the substrate of FIG. 11*c*.

FIG. 11*d* shows the rear view of the fluid transport device 1*a* of FIG. 11*c*. The electrical contacts/interface 26 can be seen on the lower surface of the substrate 2 at the end portion, which is not covered by the membrane 4 and the housing 29. The cover plate in form of a housing 29 has at is lower surface a cut-out 10.

Figure 11E:
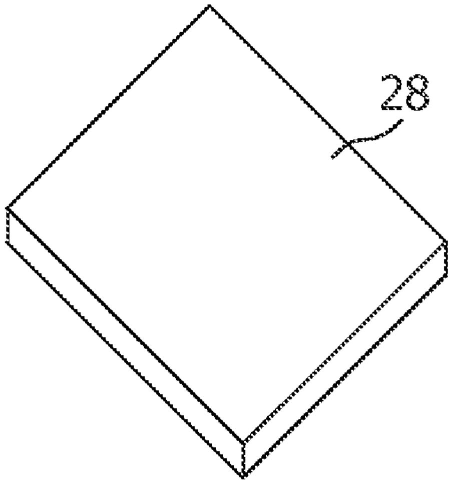
FIG. 11*e* is a sectional top view of a top element.

FIG. 11*e* shows a top view of the upper surface of a top element 28. The top element 28 can be arranged in the opening of the housing 29 to close the opening.

Figure 11F:
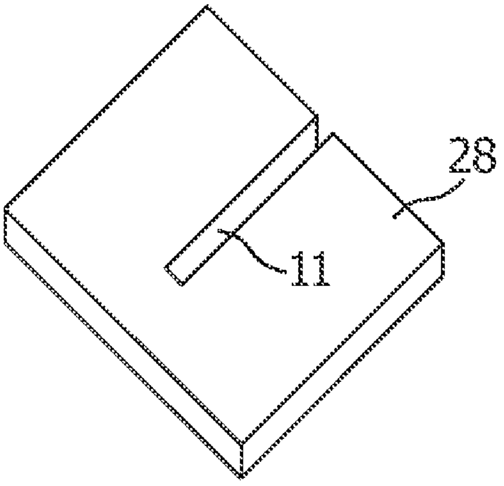
FIG. 11*f* is a sectional rear view of the top element of FIG. 11*e* with channel.

FIG. 11*f* shows the rear view of the top element 28 of FIG. 11*e*. The lower surface side of the top element 28 has a channel like recess 11. The channel like recess 11 can receive a temporally channel formed of an expanded flexible membrane section (not shown).

Figure 11G:
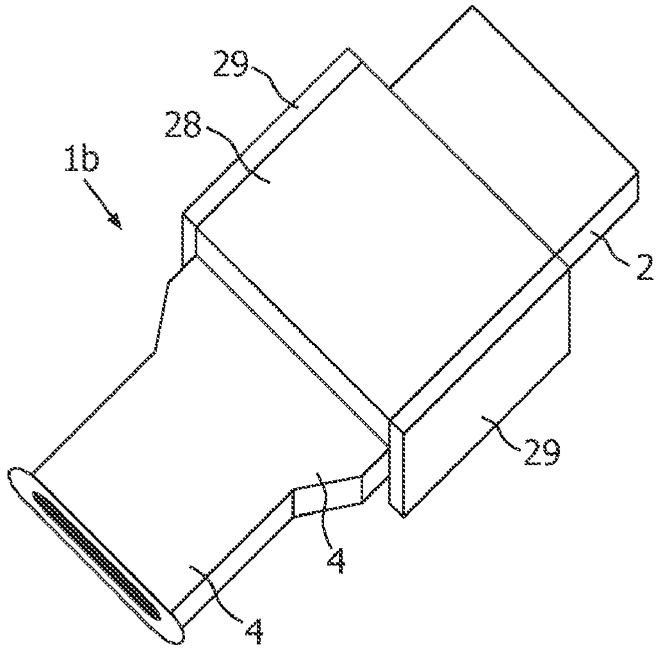
FIG. 11*g* is a sectional side view of a fluid sample transport device with no plungers.

FIG. 11g shows a top view of the fluid transport device 1*b* based on the fluid transport device 1*a* of FIG. 11*c*, whereby the top element 28 is arranged in the upper opening of the housing 29 to close the upper opening of the housing 29 and to fix the flexible membrane 4 on the substrate 2, except at the region of the channel like recess 11 (not shown).

Figure 11H:
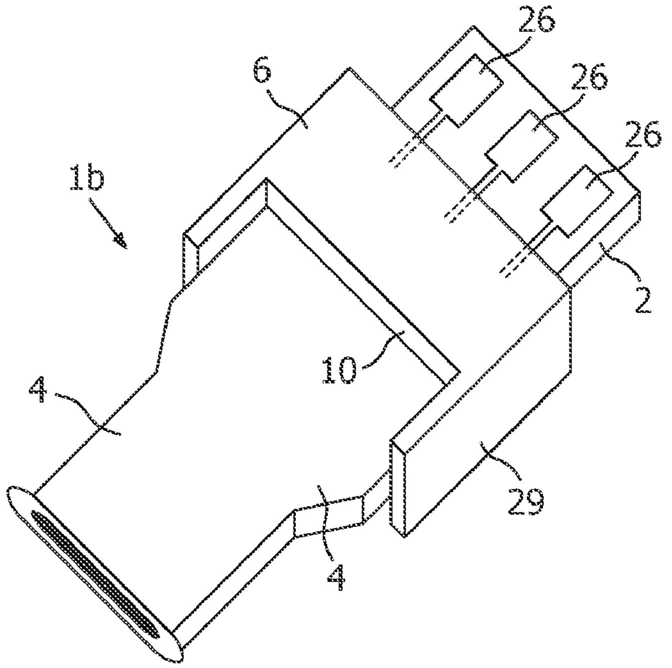
FIG. 11*h* is a sectional rear view of a fluid sample transport device of FIG. 11*g*.

FIG. 11*h* shows the rear view of the fluid transport device lb of FIG. 11*g*. The lower surface side of the top element 28 has a channel like recess 11. The channel like recess 11 can receive a temporally channel formed of an expanded flexible membrane section (not shown).

Figure 11I:
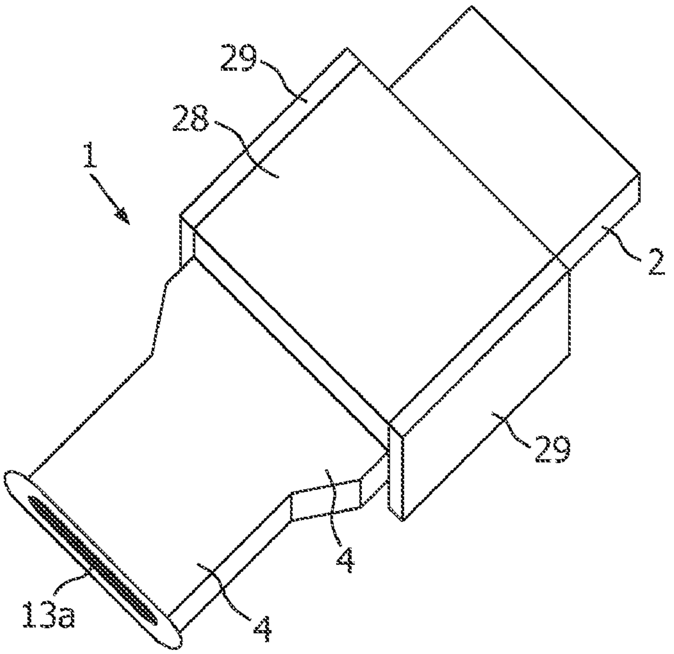
FIG. 11*i* is a sectional side view of a fluid sample transport device with plungers.

FIG. 11*i* shows a top view of the fluid transport device 1 based on the fluid transport device 1*b* of FIG. 11*g*, whereby in the cut-out (10) (not shown) of the housing 29 (cover plate 6 has the form of a housing) two plungers 5*a* and 5*b* are arranged (see FIG. 11*j* below). A fluid sample (3), for example saliva, can be brought into the opening 13*a* of the mouthpiece of the flexible membrane 4, which is wrapped around the substrate 2. The flexible membrane is pressure-fixed on the substrate by the cover plate in form of a housing 29 and the top element 28, except the membrane area facing to the channel like recess 11 of the top element 28 (not shown). The fluid sample can flow along the substrate 2 up to the section, where the fluid flow is stopped due to the valve action of the second plunger 5*b*, if the plunger 5*a* is in up-position and the plunger 5*b* is in down position. The fluid sample flow can be contacted with the reagent and analysed at the sensor, if the first plunger 5*a* is pressed down and the second plunger 5*b* is opened. Down movement of the plunger 5*a* and up-movement of the plunger 5*b* causes a fluid sample 3 transport on the substrate 2. The housing 29, top element 28 and the plungers 5*a* and 5*b* can be reused, since these elements are not contaminated with the fluid sample, where as the cartridge is disposable.

Figure 11J:
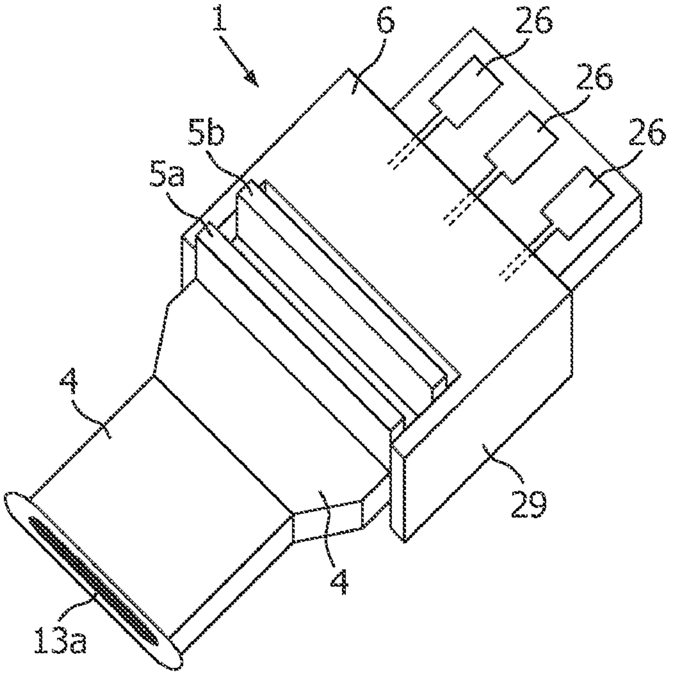
FIG. 11*j* is a sectional rear view of a fluid sample transport device of FIG. 11*i*.

FIG. 11*j* shows the rear view of the fluid transport device 1 of FIG. 11*i*. The plungers 5*a* and 5*b* are arranged in the cut-out 10 of the housing 29. The plunger 5*a* is arranged at the outer edges of the cut-out 10 and the plunger 5*b* is arranged behind the plunger 5*a*. The mouthpiece of the flexible membrane 4 has an opening 13*a* for receiving a fluid sample 3 (not shown) as described in FIG. 11*i*.

Figure 12A:
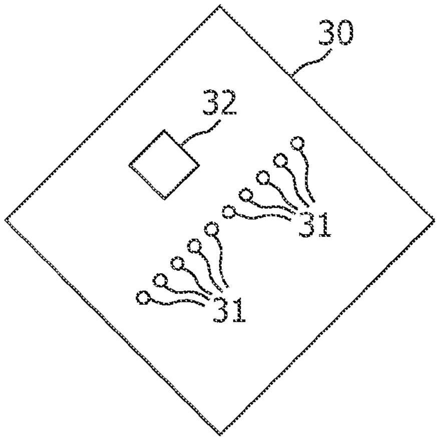

FIG. 12*a* shows a top view of a thin foil 30, also referred as thin layer. The thin foil 30 has holes 31 and cut-outs 32 for receiving at least one processing, controlling and/or detecting element (19) (not shown).

Figure 12B:
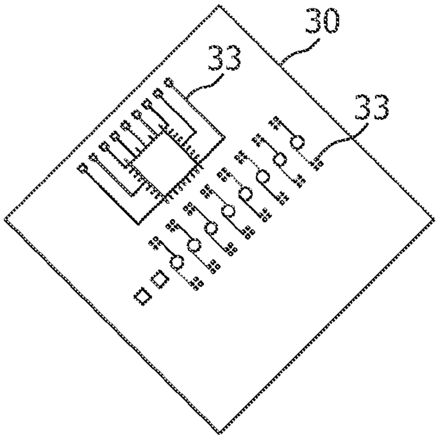
FIG. 12*b* rear view of a thin foil 30.

FIG. 12*b* shows the rear view of the thin foil 30 with integrated circuits 33.

Figure 12C:
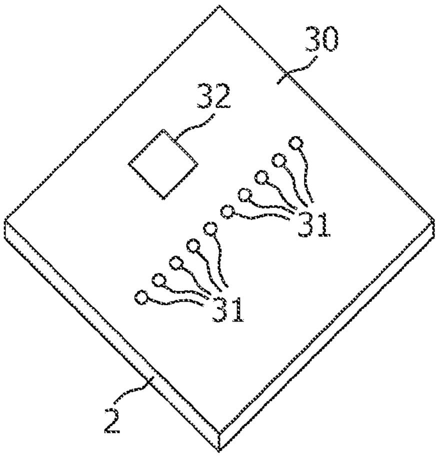

FIG. 12*c* shows a substrate 2 covered on its upper surface with a thin foil 30. The substrate 2 has through going holes 31 corresponding with the through going holes 31 of the thin foil 30. Further the cut-out 32 corresponds with the cut-out 32 of the substrate below. The cut-out 32 is formed or receiving a sensor element 19 and the holes 31 are formed for arranging therein a PCR module.

Figure 12D:
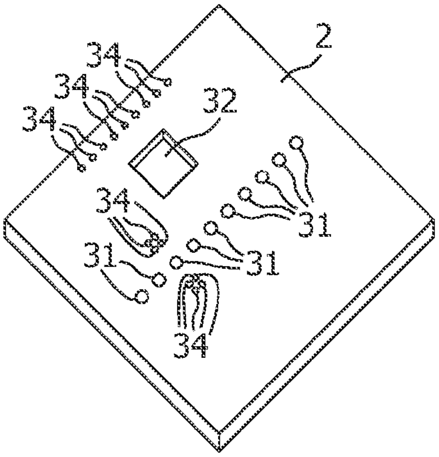
FIG. 12*d* rear view of a thin foil 30 mounted on a base substrate 2.

FIG. 12*d* shows the rear view of the substrate 2 covered on its upper surface with the thin foil 30. The substrate has at its lower surface the cut-out 32 and through going holes 31. Further, the substrate has at its lower surface ports 34 for electrical contacting the circuits 33.

The fluid sample transport device according to the present invention can be used for fluidic/electronic/mechanical devices in biomedical applications such as microTAS and LOC, biosensors, molecular diagnostics, food and environmental sensors. Further it can be used for the synthesis of chemical or biological compounds.

Preferably, the fluid sample transport device according to the present invention can be used for:

chemical, diagnostic, medical and/or biological analysis, comprising assays of biological fluids such as egg yolk, blood, serum and/or plasma;

environmental analysis, comprising analysis of water, dissolved soil extracts and dissolved plant extracts;

reaction solutions, dispersions and/or formulations analysis, comprising analysis in chemical production, in particular dye solutions or reaction solutions;

quality safeguarding analysis; and/or synthesis of chemical or biological compounds.

Manufacturing of the glass substrate and integrated functions can be provided by a four mask thin film process as known in prior art.

Examples for the manufacture of a glass substrate and integrated functions are given below:

| | |
|---|---|
| Substrate: | 0.4 mm Schott AF45 |
| Thin film processing four mask level | |
| Resistor layer: \ | 100 nm Pt, or Ti, Cr, Ni, Pt, Au, W |
| Conductor layer: | 1 micron Al or Cu, Au, Ag |
| Dielectric layer: | 0.5 micron $SiO_2$ or SiN |
| Polymer layer: | 30 micron SU8 or BCB, or other photopolymers |

Resistor elements for heater and temperature sensor are preferably made of the same thin layer such as a Pt. For the temperature-sensing element it may be important that the temperature coefficient of resistance (TCR) of the selected metal is sufficiently high.

Preferably a conductor layer of 1 micron of aluminium is used.

The combination of metals should be selected so to be compatible with the thin film dielectric layer of SiN or SiO2.

Micro channels and structures, such as areas for processing, controlling and/or detecting, are made on the substrate, preferably glass or plastic, by standard photolithographic processing using photopolymers such as SU8, supplied by MicroResist Technology, and/or BCB photopolymer supplied by Dow Chemical. However, it is most preferred the substrate as such comprises no micro channels.

Active electrical functions, such as diodes, transistors, used to control actuators and sensors can be integrated using Low Temperature Poly-Silicon (LTPS) active matrix LCD technology, as known in prior art.

To provide a comprehensive disclosure without unduly lengthening the specification, the applicant hereby incorporates by reference each of the patents and patent applications referenced above.

The particular combinations of elements and features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto. Furthermore, reference signs used in the description and claims do not limit the scope of the invention as claimed.

The invention claimed is:

1. A fluid sample transport device with reduced dead volume for at least one of processing, controlling and detecting a fluid sample, comprising:

a substrate including a cavity for holding the fluid sample, wherein an upper surface of said substrate comprises at least one processing, controlling and detecting element;

at least one flexible membrane arranged on the upper surface of said substrate;

at least one actuating element for actuating a movement of the at least one flexible membrane towards and away from the substrate to cause at least one of a fluid flow and a fluid stop the fluid flow of the fluid sample; and at least one cover plate arranged on at least one of an upper outer surface and a lower outer surface of the at least one flexible membrane;

wherein the at least one cover plate comprises at least one through going opening for receiving the at least one actuating element, so that movement of the at least one actuating element causes at least one of a pump and a valve action of adjacent areas of the at least one flexible membrane to cause the fluid flow between the upper surface of said substrate and the lower outer surface of said at least one flexible membrane, and wherein at least one temporally formed channel to direct the fluid flow of the fluid sample the substrate is temporally formed by expansion of the at least one flexible membrane into a further through going opening of the at least one cover plate in response to the at least one actuating element pushing the at least one flexible membrane into the cavity for forcing the fluid sample out of the cavity to form the at least one temporally formed channel.

2. The fluid sample transport device claim 1, wherein the at least one cover plate comprises at least one through going cut for receiving the at least one actuating element for actuating an up and/or down movement of the at least one flexible membrane in order to form a temporally membrane channel through which a fluid sample can flow through.

3. The fluid sample transport device according to claim 1, wherein the fluid transport device comprises at least one port through which a fluid sample and/or a reagent is inserted to the substrate.

4. The fluid sample transport device according to claim 1, wherein the dead volume of a total temporally formable channel volume of the fluid transport device is ≧0% and less than 10%,.

5. The fluid sample transport device according to claim 1, wherein the substrate further comprises at least one further cavity for receiving at least one of a reagent, a detecting element, a controlling element, a processing element, a waste area, a lysis and a purification area.

6. The fluid sample transport device according to claim 1, wherein the at least one cover plate possesses a plurality of through going holes for receiving plungers suitable for applying pressure or vacuum for actuating an up and down movement of the at least one flexible membrane adjacent to the lower surface of the plunger and/or a plurality of through going cuts for receiving further actuating elements suitable for applying pressure or vacuum for actuating an up and down movement of the at least one flexible membrane adjacent to the lower surface of further the actuating elements.

7. The fluid sample transport device according to claim 1, wherein the at least one flexible membrane has a thickness of 1 μm to 500 μm.

8. The fluid sample transport device according to claim 1, wherein at least one processing, controlling and detecting element comprises at least one of a control device for temperature control of the fluid sample, for heating or cooling of at least one of the fluid sample and a reagent, sensor configured to sense or modify a property of the fluid sample, an electrode, a sensor, a transducer, an optical-based device, an acoustic-based device, an electric field-based device, and a magnetic field-based device.

9. The fluid sample transport device according to claim 1, wherein the substrate comprises a base substrate, whereby the upper surface of the base substrate is covered with at least one thin foil.

10. The fluid sample transport device of claim 1, wherein the at least one temporally formed channel has a direction defined by the further through going opening of the at least one cover plate.

11. The fluid sample transport device of claim 1, wherein the at least one flexible membrane, when expanded into the further through going opening, forms a curve-like tunnel on the substrate for the fluid sample to flow through the curve-like tunnel.

12. The fluid sample transport device of claim 1, wherein the fluid sample is confined between the upper surface of said substrate and the at least one cover plate and does not contact the at least one cover plate so that the at least one cover plate is reusable.

13. The fluid sample transport device of claim 1, wherein the fluid sample is confined between the upper surface of said substrate and the at least one cover plate and does not contact the at least one cover plate and the at least one actuating element so that the at least one cover plate and the at least one actuating element are reusable.

14. The fluid sample transport device of claim 1, further comprising a further actuating element configured for insertion into the further through going opening to push on a portion of the at least one flexible membrane so that the portion contacts the upper surface of said substrate and the at least one temporally formed channel is eliminated.

15. A fluid sample transport device for at least one processing, controlling and detecting a fluid sample, comprising:

a substrate including at least one processing, controlling and detecting element, and a cavity for holding the fluid sample;

a flexible membrane arranged on an upper surface of the substrate;

an actuating element for actuating a movement of the flexible membrane; and a cover plate arranged on the flexible membrane, the cover plate having a first opening going through the cover plate, a second opening going through the cover plate, and a third opening going through the cover plate, wherein the second opening connects the first opening to the second opening;

wherein the first opening is configured to receive the actuating element for pushing a first portion of the flexible membrane into the cavity and forcing the fluid sample from the cavity to a temporally formed channel temporally formed by expansion of a second portion of the flexible membrane into the second opening, the temporally formed channel directing the fluid sample to a chamber formed by expansion of a third portion of the flexible membrane into the third opening.

16. The fluid sample transport device of claim 15, further comprising an insert for insertion in the second opening, wherein the chamber is formed by the fluid sample pushing against the third portion of the flexible membrane into the third opening in response to the actuating element pushing the first portion of the flexible membrane into the cavity and the insert pushing the second portion of the flexible membrane out of the second opening to remove the temporally formed channel and transfer the fluid sample from the cavity to the chamber through the temporally formed channel.

* * * * *